United States Patent [19]

Schwartz et al.

[11] Patent Number: 4,751,052
[45] Date of Patent: Jun. 14, 1988

[54] TUBE ALIGNMENT APPARATUS

[75] Inventors: Henry L. Schwartz, Los Gatos; Alfred H. Sturtevant, Palo Alto, both of Calif.

[73] Assignee: Sequoia-Turner Corporation, Mountain View, Calif.

[21] Appl. No.: 850,941

[22] Filed: Apr. 11, 1986

Related U.S. Application Data

[63] Continuation-in-part of Ser. No. 757,646, Jul. 22, 1985.

[51] Int. Cl.[4] ............................................. G01N 35/00
[52] U.S. Cl. .................................. 422/100; 73/864.24; 141/165; 141/177; 141/312; 422/63; 422/99
[58] Field of Search .................. 422/63, 64, 65, 23, 422/99, 100, 102, 104; 141/165, 177, 312, 372; 73/864.14, 864.25, 864.24

[56] References Cited

U.S. PATENT DOCUMENTS

| | | |
|---|---|---|
| 775,307 | 11/1904 | Ortmann et al. . |
| 1,444,540 | 2/1923 | Freedman . |
| 3,708,264 | 1/1973 | Jottier . |
| 3,879,987 | 4/1975 | Yasuhiro et al. . |
| 3,951,605 | 4/1976 | Natelson . |
| 4,040,556 | 8/1977 | Dahle . |
| 4,053,284 | 10/1977 | Posch . |
| 4,058,370 | 11/1977 | Suovaniemi . |
| 4,134,678 | 1/1979 | Brown et al. ........................ 422/67 |
| 4,271,123 | 6/1981 | Curry et al. . |
| 4,298,570 | 11/1981 | Lillig et al. . |
| 4,338,280 | 7/1982 | Ambers et al. ...................... 422/81 |
| 4,399,711 | 8/1983 | Klein . |
| 4,495,149 | 1/1985 | Iwata et al. . |
| 4,517,160 | 5/1985 | Galle et al. . |
| 4,539,855 | 9/1985 | Jacobs . |
| 4,554,839 | 11/1985 | Hewett et al. . |

FOREIGN PATENT DOCUMENTS

| | | |
|---|---|---|
| 82698 | 8/1976 | Australia . |
| 54-70236 | 12/1980 | Japan . |
| 56-2560 | 1/1981 | Japan . |
| 57-57261 | 4/1982 | Japan ................................. 422/100 |

Primary Examiner—Michael S. Marcus
Attorney, Agent, or Firm—Limbach, Limbach & Sutton

[57] ABSTRACT

An apparatus for centering the open end of tubes prior to the insertion of a probe is described. The tube aligning means has a frustoconical inner surface to gather the tube mouth held loosely in a tube rack. The tube is centered relative to the probe. The aligning means is caused to move along the probe shaft axis by cooperation of an outer probe surface and an inner female surface for receiving the probe. In the preferred embodiment, a spool-like cylindrical member is positioned within the arms of a U-shaped bracket which limits the vertical and restricts the rotational movement of the aligning member.

3 Claims, 1 Drawing Sheet

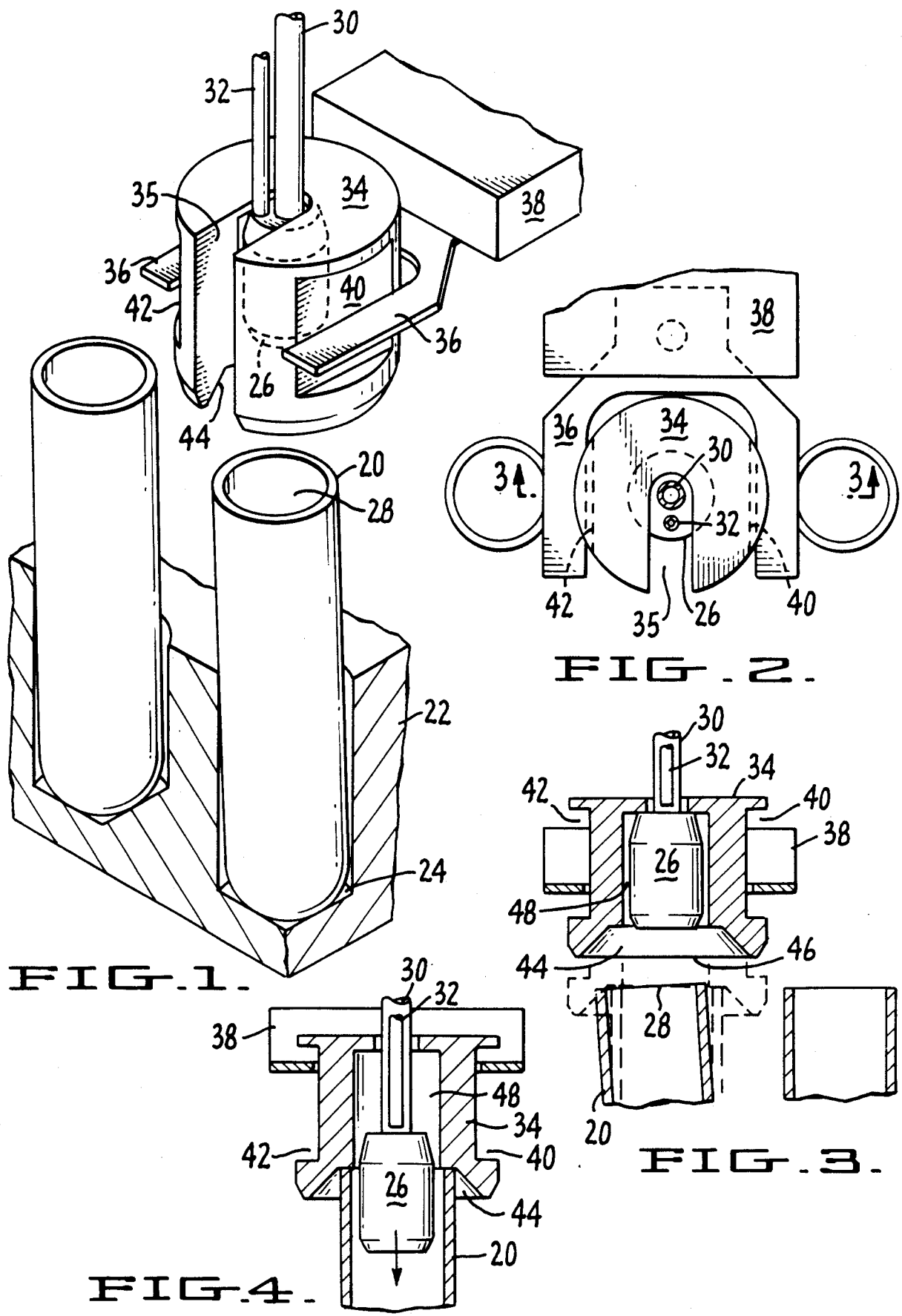

TUBE ALIGNMENT APPARATUS

This application is a continuation-in-part of our application Ser. No. 757,646 filed July 22, 1985, assigned to a common assignee.

TECHNICAL FIELD

This invention relates generally to automated sampling and analysis and the use of probes to accomplish such analyses and more specifically to a tube-aligning device which centers the tube opening prior to the insertion of a probe into the tube.

BACKGROUND OF THE INVENTION

The automation of immunoassay techniques has spawned a series of inventions without which such automated equipment would sometimes fail. The sensitivity of immunoassay techniques requires that unbound material be completely removed to permit detection. In practice this translates to providing washing techniques which are good to the parts per million level. When practiced manually, this washing procedure could be repeated several times or each individual wash could be extended over a greater period of time. The automation of this procedure makes soaking for an extended period of time impractical.

To overcome the difficulty of providing sufficient washing in a practical period of time, a wash probe has been developed to accomplish a high fluid throughput in a short time interval which vigorously injects the fluid to improve "wash" quality. The resulting probe is of substantial outside diameter, approaching the inside diameter of the test tubes in which such assays are typically performed. The use of this probe to remove unreacted reagents is the subject of our application Ser. No. 06/757,525 entitled METHOD AND APPARATUS FOR REMOVING UNREACTED COMPONENTS IN AUTOMATED IMMUNOASSAY TECHNIQUES, assigned to a common assignee.

While this increased probe size solved problems associated with automated washing procedures, the size of the probe in relation to the tube mouth made reliable entry into the tube a difficult problem. The wash probe, which is moved vertically by a shaft, must enter a series of tubes without getting caught on the edge of any tube. The test tubes are maintained in a rack which is not accurately made, and holds the tubes only loosely. Since the probe has a diameter close to that of the tube it must enter, an apparatus is needed to insure that the probe goes cleanly into the tube.

The subject invention provides a tube alignment apparatus which aligns the tube held loosely by the rack, centers the tube mouth relative to the probe and thereby permits effective and accurate insertion of a probe.

It is therefore an object of this invention to provide a tube alignment apparatus which permits accurate insertion of a probe, whose outside diameter is relatively large in comparison to the inside diameter of the receiving tube, into a receiving tube.

It is further an object of this invention to provide an inexpensive means to enable automated use of a large wash probe capable of accomplishing the degree of washing required in immunoassay techniques in a short period of time.

It is another object of this invention to provide a simple way to center test tube mouths which is effective and inexpensive.

It is a still further object of this invention to provide a device which requires no alignment or adjustment separate from the probe alignment since it is guided by the probe.

These, and further objects, shall become apparent to those skilled in the art by reference to this specification and the drawings to which it refers.

SUMMARY OF THE INVENTION

In a sampling apparatus, a probe is connected to a shaft which moves the probe relative to a rack of tubes. This invention provides an improvement which comprises a tube aligning means for centering a tube mouth prior to insertion of the probe. The tube aligning means has a frustoconical interior surface to interact with a tube which is loosely held in a rack. Also provided is a probe receiving means which has an inner female surface configured to fit loosely around the probe. The aligning means is caused to move along the shaft of the probe since the tube aligning means and probe receiving means are attached. When the probe is moved up or down the tube alignment means moves also.

In a preferred embodiment the outside cylindrical surface of the aligning means has two diametrically opposed slotted surfaces. Received within the slotted surfaces are the arms of a U-shaped bracket which is fastened at its closed end to a fixed member. The bracket prevents rotational movement of the probe receiving means relative to the shaft. The cooperation of the bracket and slotted surfaces also limits movement of the probe receiving means along the shaft longitudinal axis. A radial slot is provided in the tube alignment means and the probe receiving means to permit installation of the apparatus after the probe has been affixed to the shaft.

BRIEF DESCRIPTION OF THE DRAWINGS

FIG. 1 is a perspective view of the tube alignment apparatus of the instant invention and the wash probe.

FIG. 2 is a top view of the tube alignment apparatus.

FIG. 3 is a cross section taken along the line 3—3 in FIG. 2.

FIG. 4 is another cross section taken along the line 3—3 in FIG. 2 but shows the probe inserted in a centered tube.

DETAILED DESCRIPTION OF THE INVENTION

In the development of this invention, it was recognized that in view of the increased probe size required to effect the necessary fluid additions and suctions in a short time cycle, it was necessary to insure that the tube mouth was properly aligned with the probe to prevent the probe from hanging up on the tube mouth when it was inserted into the tube. A tube aligning means is used to gather in the loosely held tube and center the tube to coincide with the longitudinal axis of the shaft-probe. The aligning means has a frustoconical inner surface to accomplish this centering. The frustoconical inner surface permits gradual movement of the tube as it contacts the aligning means. The altitude of the frustoconical member is positioned along the shaft longitudinal axis so that the tube will be properly centered when contained within the inner frustoconical surface of the aligning means.

The aligning means is caused to move along the shaft longitudinal axis by a probe receiving means. The principle advantage of this relationship is that the aligning means needs no alignment or adjustment separate from the probe. The probe receiving means has an inner female surface which is configured to receive the outer surface of the probe. Thus, when the probe is in a retracted position, the receiving means and probe are in contact, causing the aligning means to also be disposed in a retracted position. When the probe is extended by the action of the shaft, it carries with it the receiving means so that the aligning means is also caused to extend. The geometrical configuration of the probe receiving means is related to the probe shape. Other than the necessary male-female type relationship between the receiving means and the probe, any number of shapes will suffice and are intended to be within the scope of the appended claims.

Further, the external surfaces of the tube aligning means can be chosen from a wide variety of geometrical shapes. These external surfaces must house the frustoconical interior surface, be compatible with the tube-holding rack and address other machine-design parameters which would be apparent to those skilled in the art.

Depending upon the tube rack and tube translation relative to the probe, the aligning means may need to be limited in its range of movement along the shaft longitudinal axis, particularly when a tube location is empty. In this circumstance, lacking a range limitation, it would be possible for the aligning means to extend fully with the probe, causing the aligning means to contact the tube rack. If this occurs, it is possible that the tube aligning means could become jammed in the rack, causing difficulty when the probe retracts. In the preferred embodiment described below, a spool-like external surface and a U-shaped bracket are used to limit the range of movement, but it will be apparent to those skilled in the art that other embodiments of this limiting means are possible which fall within the scope of the appended claims.

It should be noted that while the preferred embodiment utilizes a matrix tube rack having rows and columns, the subject invention can be used in conjunction with any sort of tube holder. Also, it will be recognized by those skilled in the art that the subject invention is universally applicable to any system in which tubes are positioned under a probe regardless of whether only tubes move, the probe moves or both move.

It will also be recognized by those skilled in the art that this invention has application to a broader context than immunoassay probes and test tubes. In essence, the present invention permits the accurate insertion of a member into a tube or bottle or pipe whose inside diameter is relatively close to the outside diameter of the member. So, for example, this invention has application in the bottling industry wherein the filling tube diameter approaches the bottle opening diameter Therefore, when the terms probe and tube are used hereinafter and in the claims they are to be interpreted more broadly than in the specific case of the preferred embodiment involving probes and sample tubes.

Turning now to the preferred embodiment, FIG. 1 shows a test tube 20 being loosely held in a rack 22. A hole 24 in rack 22 is typically chosen to have a diameter slightly larger than tube 20 to make placement and replacement of tube 20 easy and convenient. This play in the tube diameter to hole diameter relationship makes insertion of wash probe 26 into a tube mouth 28 difficult to automate because of the relatively similar diameters of tube mouth 28 and probe 26 When probe 26 is positioned above tube mouth 28, if the tube mouth 28 is not properly aligned with the probe 26, probe 26 might become hung up on the mouth 28 when the probe 26 is moved in the vertical axis by action of shaft 30. To prevent this hanging up, tube aligner 34 is provided to center tube mouth 28 prior to insertion of probe 26. Tube aligner 34 has a slot 35 which permits tube aligner 34 to be installed after probe 26 has been installed at the end of shaft 30. Tube aligner 34 is held in place, relative to probe 26, by a U-shaped bracket 36. This bracket 36 is affixed to a carriage member 38 from which carriage probe 26 is also suspended. The carriage, in this embodiment, acts to translate the probe 26 in the horizontal axes and vertical axis relative to the tubes. Other means for accomplishing this result will be apparent to those skilled in the art, depending upon the dynamics of the probe-shaft system. Bracket 36 cooperates with slotted sections 40 and 42 in tube aligner 34 side walls.

Referring now to the top view shown in FIG. 2, the relationship between bracket 36 and tube aligner 34 can be more fully described Bracket 36 is affixed to the carriage member 38. Carriage member 38 is part of the motor driven carriage assembly (not shown in this figure) which causes probe 26 to move in the horizontal and vertical axes. By fastening bracket 36 to the carriage, its coordinates are fixed relative to probe 26.

Tube aligner 34 has two diametrically opposed sections cut away, slotted sections 40 and 42. From FIG. 2, it can be seen that bracket 36 is received within slotted sections 40 and 42. It is important to note, however, that slotted sections 40 and 42 do not run the entire vertical length of tube aligner 34. Instead, these slots create a spool-like member so that aligner 34 can only move a pre-selected vertical distance relative to bracket 36 before the top or bottom surfaces of the slotted sections come into contact with bracket 36. In this manner, bracket 36 supports tube aligner 34 when the probe 26 lowers down into a position where there is no tube in the hole in the rack. This prevents aligner 34 from becoming jammed in the tube rack 22 when no tube is present in the subject hole. Bracket 36 also prevents aligner 34 from rotating in operation which could cause the aligner 34 to jam on the detergent dispenser 32. Finally, bracket 36 serves as a retainer to prevent aligner 34 from escaping due to slot 35.

Aligner 34 has a radial slot 35 which runs the length of the aligner. Slot 35 permits sufficient clearance for the detergent dispenser 32 which is located just off center and forms a part of probe 26.

The dynamics of this aligning device are shown in FIGS. 3 and 4. In FIG. 3, an outer surface of probe 26 holds aligner 34 just above tube 20. Tube 20 is not properly positioned with tube mouth 28 being off center from the vertical axis of probe 26. The dotted lines in FIG. 3 represent a properly aligned tube 20 and aligner 34. In FIG. 3, probe 26 is in the retracted position At the bottom of aligner 34 is a hollow frustoconical section 44 whose basal face opens at the aligner's bottom surface 46. Just above this hollow frustoconical section 44 is a second hollow, cylindrical section 48, in this embodiment the probe receiving means. When probe 26 is retracted, it is positioned in cylindrical section 48, the probe's outer surface in contact with a lower inner surface of section 48. As probe 26 is lowered by shaft 30, so too is aligner 34. Aligner 34 weighs about 1.25 ounces in this embodiment. This weight is sufficient to move tube 20 in its rack in order to center the tube mouth 28 to be directly in line with the vertical axis of probe 26.

Referring to FIG. 3, it can be seen how the aligner 34 centers the tube mouth 28. The open end of tube 20 is received within the frustoconical section 44. The inclined faces of this frustoconical section 44 gather in the tube mouth 28. The tube mouth 28 can move in its hole so that the tube mouth 28 can be completely in contact with the upper surface of frustoconical section 44. This contact insures that the longitudinal axis of tube 20 is coincident with the longitudinal axis of probe 26 thereby avoiding hanging the probe 26 up on the tube mouth 28. Once the tube 20 is properly aligned with probe 26 and shaft 30, the probe 26 can be inserted in tube 20 to accomplish the desired fluid dispensing and suction steps. Upon completion of the process, the probe 26 is activated by the carriage and retracted from tube 20. The vertical movement of probe 26 along shaft 30 also causes the aligner 34 to retract into the position illustrated in FIG. 3. The carriage then translates the probe 26 and aligner 34 in the horizontal plane, coming to rest over the next tube in the rack.

The top of probe 26 fixes the rotational and vertical movement of aligner 34. The bracket 36 is received by slotted sections 40 and 42. In this embodiment, the slotted sections 40 and 42 are cut on opposite side of the cylindrical member 34. They only run across a small portion of the external surface of the overall cylindrical aligner 34. The cooperation of the bracket 36 and slotted sections 40 and 42 prevents the aligner 34 from rotating about the shaft 30. With respect to vertical movement, the height of the aligner 34 represents the maximum vertical movement permitted by bracket 36. At the top and bottom of slotted sections 40 and 42, there are lips which will catch the bracket 36 and thereby limit further movement in the shaft longitudinal axis. This is important, for example, if the probe 26 comes to rest over a hole in the rack in which there is no tube. Thus, when probe 26 is lowered, bracket 36 comes into contact with the upper lip of sections 40 and 42 and stops the aligner 34 from traveling any further in the longitudinal axis.

While the subject invention has been described with respect to a particularly preferred embodiment it will be apparent to those skilled in the art that modifications and variations may be made which are still intended to be within the scope of the appended claims.

We claim:

1. An apparatus for registering a tube with a probe prior to insertion of the probe into a tube which comprises
   a barrel-shaped probe subtended from a cylindrical shaft;
   a U-shaped bracket; and
   a spool-like restraint member having tangential, outer surface slots and a frustoconical interior surface which freely communicates with top and bottom surfaces of the restraint member and a radial slot through said restraint member disposed along an altitude of said frustoconical surface;
   wherein said barrel-shaped probe is received within said restraint-member interior surface and selectively contacts an upper interior portion of said surface and wherein said U-shaped bracket is received in said tangential outer surface slots to hold said restraint member within a range which is defined by restraint member upper and lower surfaces and to permit limited movement of said restraint member only along an altitude of said frustoconical surface.

2. In an apparatus having an elongate probe appended to one end of a shaft for selectively inserting and withdrawing the elongate probe relative to a tube, said probe and shaft having a longitudinal axis
   the improvement comprising:
   tube aligner means for centering a tube mouth prior to insertion of the elongate probe into a tube, said aligner means having a frustoconical inner surface;
   limiting means for restricting to a selected range the movement of the tube aligner means along the shaft longitudinal axis;
   means for receiving an outer surface of the elongate probe; and,
   a radial slot in said tube aligner means and in said probe receiving means, said slot being disposed along a line parallel to the probe longitudinal axis, and said slot adapted to receive said probe and shaft
   wherein said tube aligner means is contiguous with said probe receiving means along the probe longitudinal axis and which aligner means is caused to move selectively in the shaft and probe longitudinal axial direction by the cooperation of said probe outer surface receiving means and the outer surface of the probe.

3. In an apparatus having an elongate probe appended to one end of a shaft for selectively inserting and withdrawing the elongate probe relative to a tube,
   the improvement comprising:
   tube aligner means for centering a tube mouth prior to insertion of the elongate probe into a tube, said aligner means having a frustoconical inner surface and a slotted outer surface to create a spool-like outer shape to receive arms of a U-shaped bracket;
   a U-shaped bracket, whose position is fixed in space relative to the shaft, probe and tube aligner means, having a closed end and two arms for receiving said tube aligner means slotted, spool-like outer surface;
   means for receiving an outer surface of the elongate probe; and,
   a radial slot in said tube aligner means and in said probe receiving means, said slot being disposed along a line parallel to the probe longitudinal axis, and said slot adapted to receive said probe and shaft
   wherein said tube aligner means is contiguous with said probe receiving means along the probe longitudinal axis and which aligner means is caused to move selectively in the shaft and probe longitudinal axial direction by the cooperation of said probe outer surface receiving means and the outer surface of the probe, and wherein the cooperation of said U-shaped bracket and spool-like tube aligner means outer surface restricts rotational movement of said tube aligner means about said shaft and probe and which further restricts the movement of the tube aligner means along the shaft longitudinal axis to a selected range substantially equivalent to the width of the tube aligner outer surface slots.

* * * * *